(12) United States Patent
Berners et al.

(10) Patent No.: US 9,574,976 B2
(45) Date of Patent: Feb. 21, 2017

(54) DEVICE AND METHOD FOR TRANSPORTING AND PREPARING CELLULAR MATERIAL

(76) Inventors: Otto Berners, Heidelberg (DE); László Fiac Vass, Budapest XV (HU)

( * ) Notice: Subject to any disclaimer, the term of this patent is extended or adjusted under 35 U.S.C. 154(b) by 0 days.

(21) Appl. No.: 13/702,892

(22) PCT Filed: May 12, 2011

(86) PCT No.: PCT/DE2011/001068
§ 371 (c)(1),
(2), (4) Date: Jan. 4, 2013

(87) PCT Pub. No.: WO2011/153986
PCT Pub. Date: Dec. 15, 2011

(65) Prior Publication Data
US 2013/0203102 A1    Aug. 8, 2013

(30) Foreign Application Priority Data
Jun. 9, 2010   (DE) .................. 10 2010 023 229

(51) Int. Cl.
*G01N 1/34*   (2006.01)
*B01L 3/00*   (2006.01)
(Continued)

(52) U.S. Cl.
CPC ............. *G01N 1/34* (2013.01); *B01L 3/5021* (2013.01); *B01L 3/5029* (2013.01);
(Continued)

(58) Field of Classification Search
CPC ........... G01N 1/34; G01N 1/40–1/4005; B01L 2300/045–2300/047; B01L 3/50–3/5023;
(Continued)

(56) References Cited

U.S. PATENT DOCUMENTS 7,270,959 B2 *   9/2007   Hudak ................. B01L 3/502
                                                            422/537
2003/0175166 A1 *   9/2003   Schluter .................. 422/101
(Continued)

FOREIGN PATENT DOCUMENTS

| EP | 0 298 513 | 1/1989 |
| EP | 2 014 367 | 1/2009 |
| WO | WO 01/88501 | 11/2001 |

OTHER PUBLICATIONS

European Patent Office English machine translation of DE3719302 with original document; translation generated Jan. 7, 2016.*

*Primary Examiner* — Ralph Gitomer
*Assistant Examiner* — Trent Clarke
(74) *Attorney, Agent, or Firm* — Cozen O'Connor

(57) ABSTRACT

Embodiments of the invention relate to a device for transporting and preparing cellular material in a fluid for subsequent diagnostic purposes, comprising a cylinder having a fluid-tight screw-on cap and a fluid-tight base part that can be screwed off of the cylinder. The cap can be screwed onto the base part in a fluid-tight matter. The device provides for introducing cellular material to be diagnosed into a fluid in the cylinder, closing the cylinder by a cap for transport, removing the cap, introducing a filter device and concentrating the cellular material on a filter surface, after which the fluid level is at that part of the base part below the connection to the cylinder, disposing of the filtrate, removing the base part, pressing the filter surface onto an object carrier for a cell analysis, and closing the base part by the cap for further transport.

6 Claims, 5 Drawing Sheets

(51) Int. Cl.
*G01N 1/40* (2006.01)
*G01N 1/28* (2006.01)

(52) U.S. Cl.
CPC ...... *G01N 1/4077* (2013.01); *B01L 2200/026* (2013.01); *B01L 2300/0681* (2013.01); *G01N 1/2813* (2013.01); *G01N 2001/4088* (2013.01)

(58) Field of Classification Search
CPC ..... B01L 2300/0681; B01L 2300/0832; B01L 2400/0478
USPC ...................................................... 435/307.1
See application file for complete search history.

(56) References Cited

U.S. PATENT DOCUMENTS

2008/0173183 A1\* 7/2008 Chen ............................... 99/285
2009/0007937 A1\* 1/2009 Chen et al. ..................... 134/10

\* cited by examiner

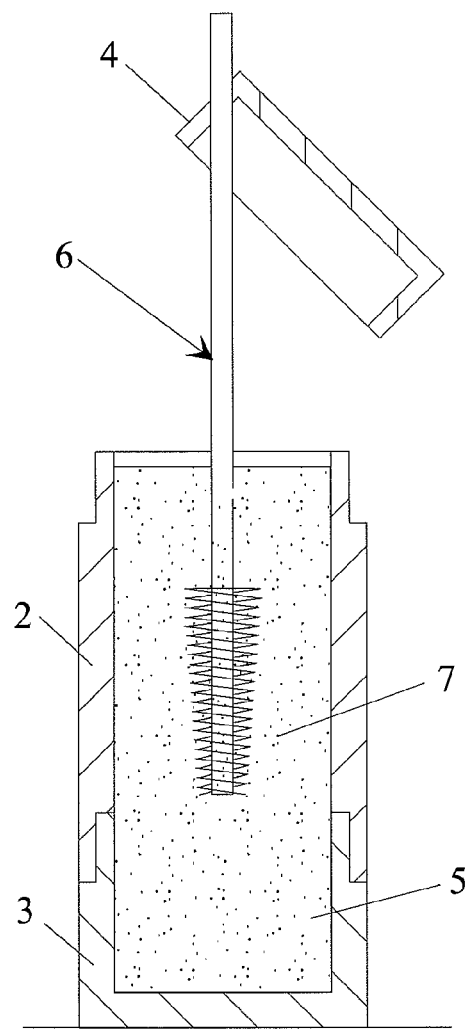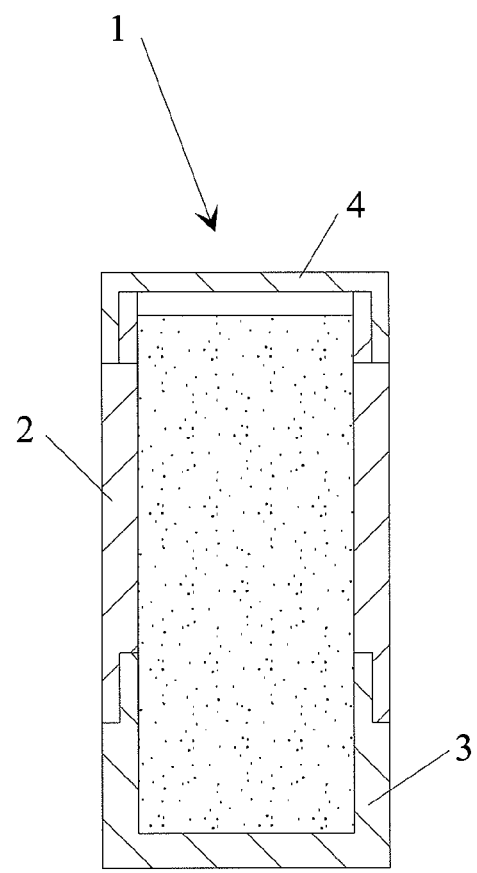
Fig. 1                    Fig. 2

DEVICE AND METHOD FOR TRANSPORTING AND PREPARING CELLULAR MATERIAL

CROSS-REFERENCE TO RELATED APPLICATIONS

This is a U.S. national stage of application No. PCT/DE2011/001068 filed 12 May 2011. Priority is claimed on German Application No. 10 2010 023 229.7 filed 9 Jun. 2010, the content of which is incorporated herein by reference in its entirety.

BACKGROUND OF THE INVENTION

1. Field of the Invention

The invention relates to a device and a process for transportation and preparation of cell material in a liquid for following diagnostic purposes.

2. Description of the Related Art

Human Papillomaviruses, abbreviated HPV, represent a group of more than 100 known wart viruses. A multitude of these viruses are classified as cancer causing, as they are participating in the development of not only cervical cancer but also of cancer of the penis, the vulva, the anus and the mouth.

About 15 virus types are classified as high risk viruses for causing cervical cancer. Thirteen of these viruses are responsible for about 30% of the cancer cases. Vaccination against two of the viruses, which are responsible for 70% of the cancer cases, is now possible.

In the case of a HPV-infection, an early and accurate identification of the infection causing the virus is necessary based on extensive screening processes, because this allows for advanced diagnostic testing and for related therapy strategies to be developed.

Recent findings show that a diagnosis of highest safety standard combines a morphological and a bio-molecular cell investigation. Experts assume that for early cancer detection more importance will be attached to the combined diagnostic based on the investigation of the cell morphology and a specific HPV-test.

SUMMARY OF THE INVENTION

An object of the invention is to provide a device and a process for the transportation and the preparation of cell material in a liquid for subsequent diagnostic purposes, which allows, in a simple and cost-effective way such combined diagnostic processes.

The technical problem is solved in accordance with embodiments of the invention by a cylinder with a liquid-tight twist cap and with a bottom part that is liquid-tight connected with the cylinder and can be screwed off the cylinder, whereby the cap is suitable to be selectively screwed-on a top part of the cylinder and to the bottom part.

This three-part container-like device according to embodiments of the invention provides a set of advantages. The device may be made of plastic or metal, and allows for cost-effective production. In particular the device provides a first transport container with a comparatively big volume, in which the cell-containing liquid can be transported safely.

An additional container will be built later by the bottom part, which is screwed off the cylinder and closed by the cap, whereby a reduced volume is available for a further transportation or storage of the cell material in the liquid.

Besides providing an especially low-cost one-way transportation instrument the device is, according to embodiments of the invention, suitable for the preparation of the cell material to be investigated. Hereto, a filter device is designed with a tube accurately radially fitting into the cylinder. The tube is open at one end and at the other end closed by a filter, which at least partly sticks out of the tube.

By pushing the filter device into the cylinder with the connected bottom part, the liquid penetrates the filter, and cell material will be concentrated at the filter surface. This concentrated cell material can, after removing the bottom part, be directly pressed on a slide.

Such print-processes are principally known and explained for example in WO 01/88501.

In order to allow the removal of the bottom part without problems by screwing, the penetration depth and the geometry of the end of the filter device are designed such that when the filter device is inserted the liquid level in the bottom part will be below the connection of the bottom part to the cylinder. By this measure it will be assured that no liquid spills out of the cylinder after screwing off the cylinder with the filter device.

Hereto, a radial extended ring shoulder can be provided at the open end of the tube, which serves as an arrestor and at the same time as an operating handle.

The use of the device according to embodiments of the invention is explained in the following. It is an advantage that the device is already a closed and off-the-shelf transport container from the production side, which can be filled with a liquid for conservation and, if applicable, disaggregation of the cell material from a swap or suchlike.

After screwing off the cap, the diagnostic cell material can be inserted into this liquid, e.g. by washing off the material from a sample brush or spatula.

After closing the cylinder by a cap of the device, the device is ready for shipment to a laboratory.

At a laboratory for diagnostic testing, the cap is removed and the filtration device pushed into the cylinder. At this filtration device, as described above, an axial filter sticks out, so that by pushing the filter device a concentration of cell material at the filter surface takes place. When the filter device is pushed into the cylinder with the bottom part, the level of the cell containing liquid in the bottom part is lowered to such an extent that it is below the connection of the bottom part with the cylinder.

After the disposal of the filtrate out of the end of the filter device, the bottom part can be removed without spilling the liquid.

The bottom part with the cell containing liquid can then be closed, and the material is available for other investigations in other laboratories or for storage.

The cell material concentrated on the filter surface is also available for subsequent investigations after stamping it on the slide.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The device and the process according to embodiments of the invention are explained in more detail by reference to the drawings, in which schematically an example of operation of the device is given.

FIG. 1 shows the inserting of cell material into the device according to one embodiment of the invention;

FIG. 2 shows a closed device for transportation;

DETAILED DESCRIPTION OF THE PREFERRED EMBODIMENTS

Figures 3, 4:
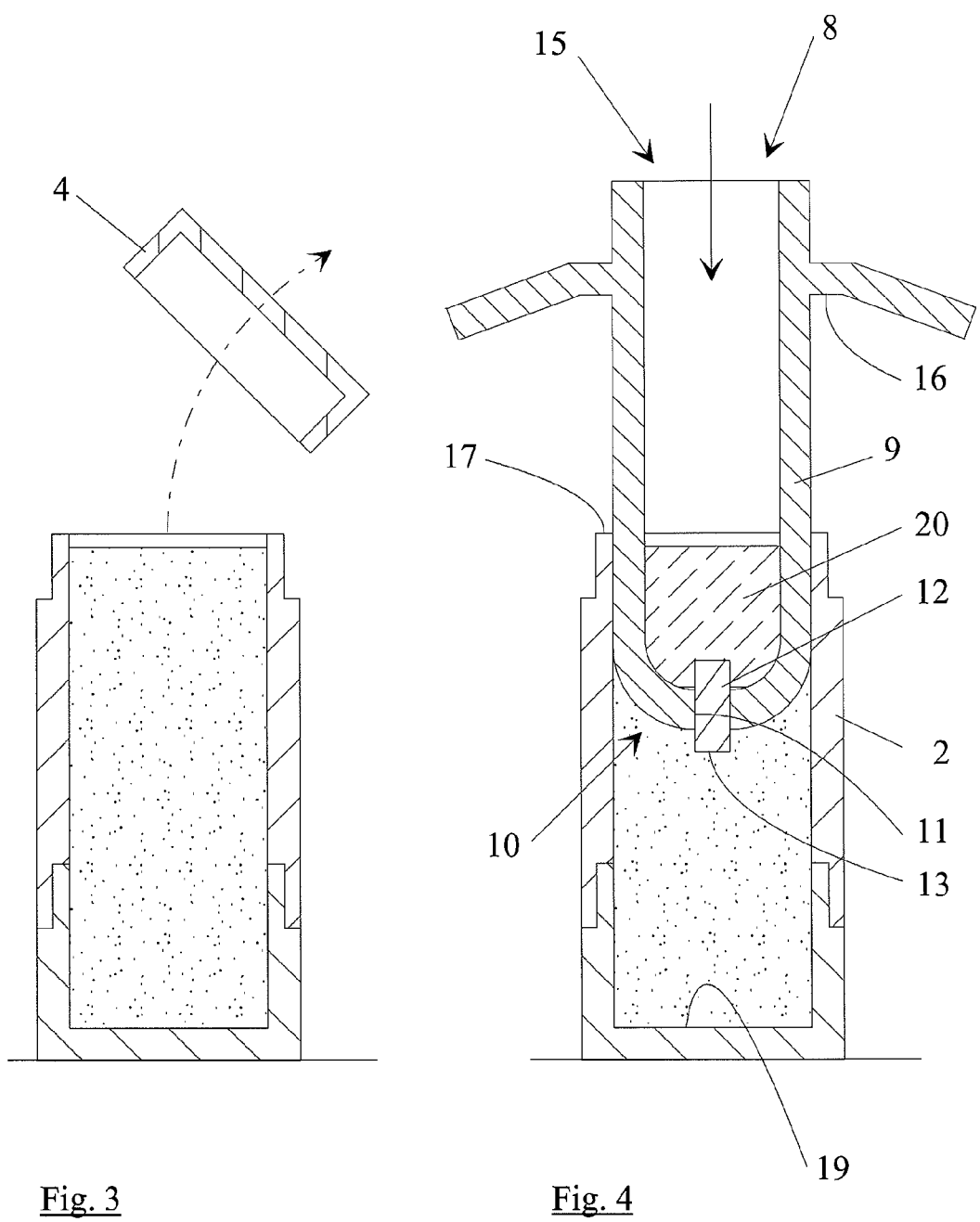
FIG. 3 shows the removal of the cap.
FIG. 4 shows the inserting of a filter device.

FIG. 1 shows the device 1 according to an embodiment of the invention with a cylinder 2, and a bottom part screwed onto a lower part of the cylinder. Sealing can be achieved merely by the winding. If applicable, standard sealing measures like an O-ring gasket can be used.

The device 1 can be supplied with a screwed-on cap 4 and filled with a liquid 5, which is suitable to conserve the cell material 7 especially for transportation. The cell material may be inserted by a sample taking instrument, here in form of a sample-taking-brush 6, for example.

Such transportation is possible without problems, if according to FIG. 2, the sample-taking-brush 6 is removed and the device 1 is closed liquid-tight by the cap 4.

Shipped to a laboratory, the cap 4 will be removed, as shown in FIG. 3, and a filter device 8 will be inserted into the cylinder 2, as shown in FIG. 4.

The filter device 8 includes a tube 9, which can be inserted into the cylinder 2 and which is accurately radially fitting into the cylinder 2. The lower end 10 of the tube 9, inserted in cylinder 2, is widely rounded and closed, with a central penetration 11 in which a filter 12 sticks out of the tube 9. This filter 12 has a generally radially extending filter surface 13.

Figure 5:
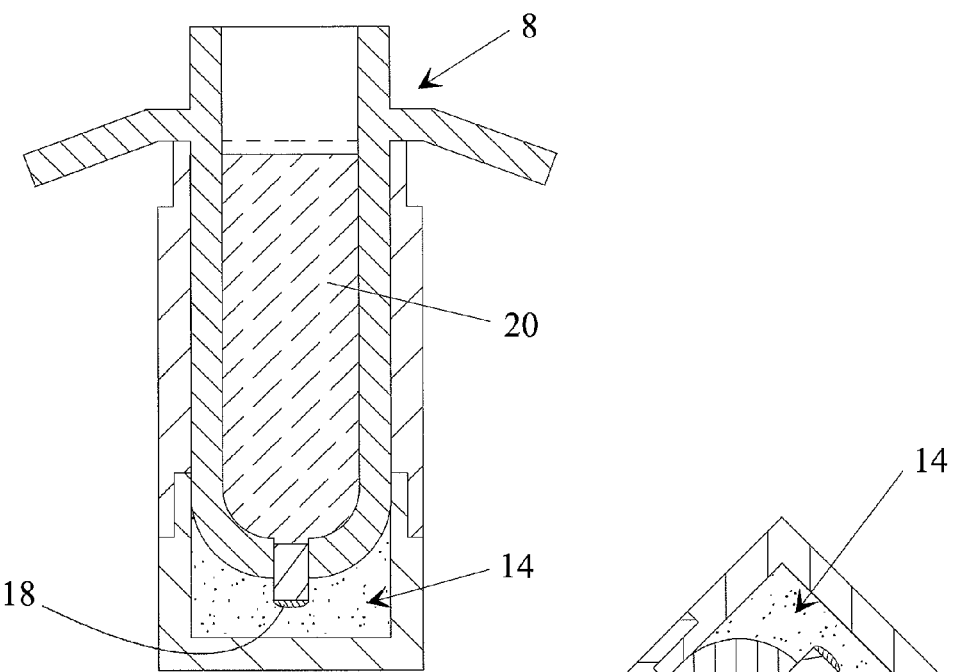
FIG. 5 shows a completely inserted filter device.

Furthermore, the end 10 of the tube 9 with the filter 12 is designed so that after complete insertion of the tube 9 into the cylinder 2, as shown in FIG. 5, a leftover 14 of the liquid with the cell material stays in the bottom part 3 and the cylinder 2. The volume of the leftover liquid is measured less than the inner volume of the bottom part, approximately 0.5 ml to 1.5 ml.

To assure this, the open end 15 of the tube 9 can be designed with a radially extending ring-shoulder 16, which serves as an arrestor on the upper rim 17 of the cylinder 2. In addition, such a ring-shoulder 16 eases the handling of the filter device 8.

Furthermore, by these measures it will be assured that the filter surface 13 with the concentrated cell layer 18 is not touching the bottom of the bottom part 3.

Figure 6:
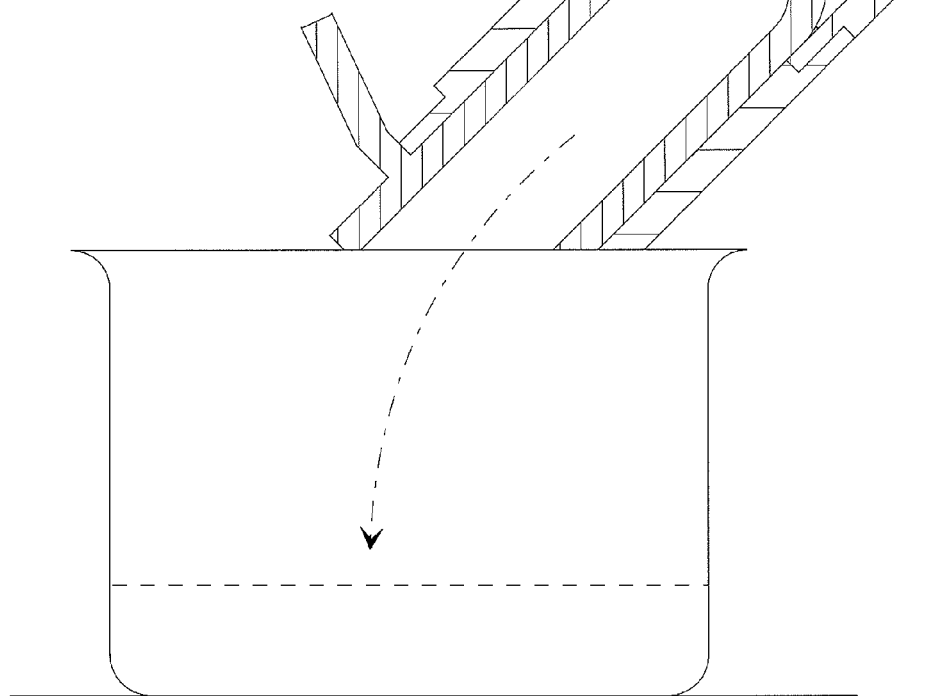
FIG. 6 shows the removal of the filtrate.

The upper end 15 of the tube is open, so that the filtrate 20 can be disposed as shown in FIG. 6 without problems. Thereby, the rest 14 of the liquid with cell material stays in the device 1.

Figure 7:
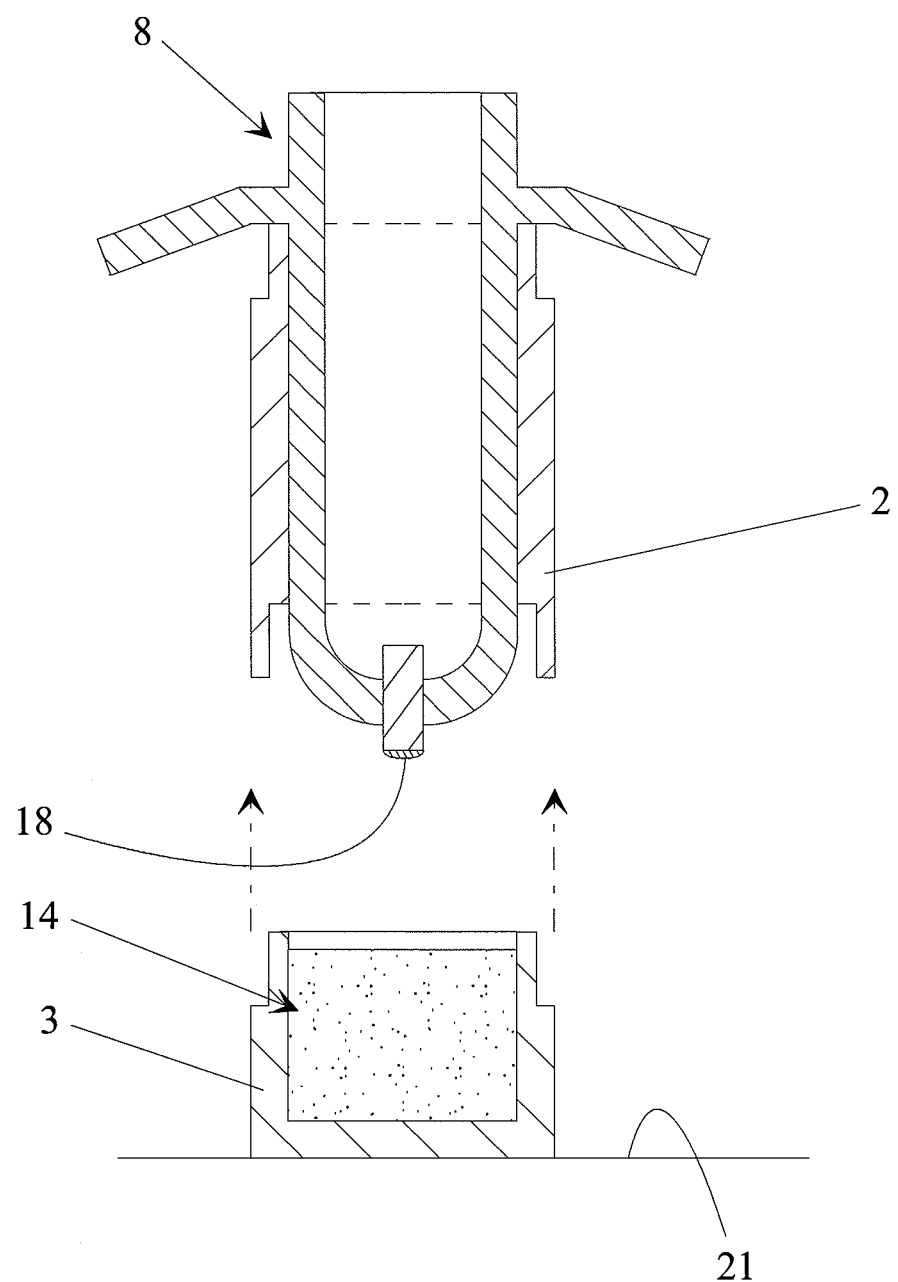
FIG. 7 shows the removal of the bottom part.
Figure 8:
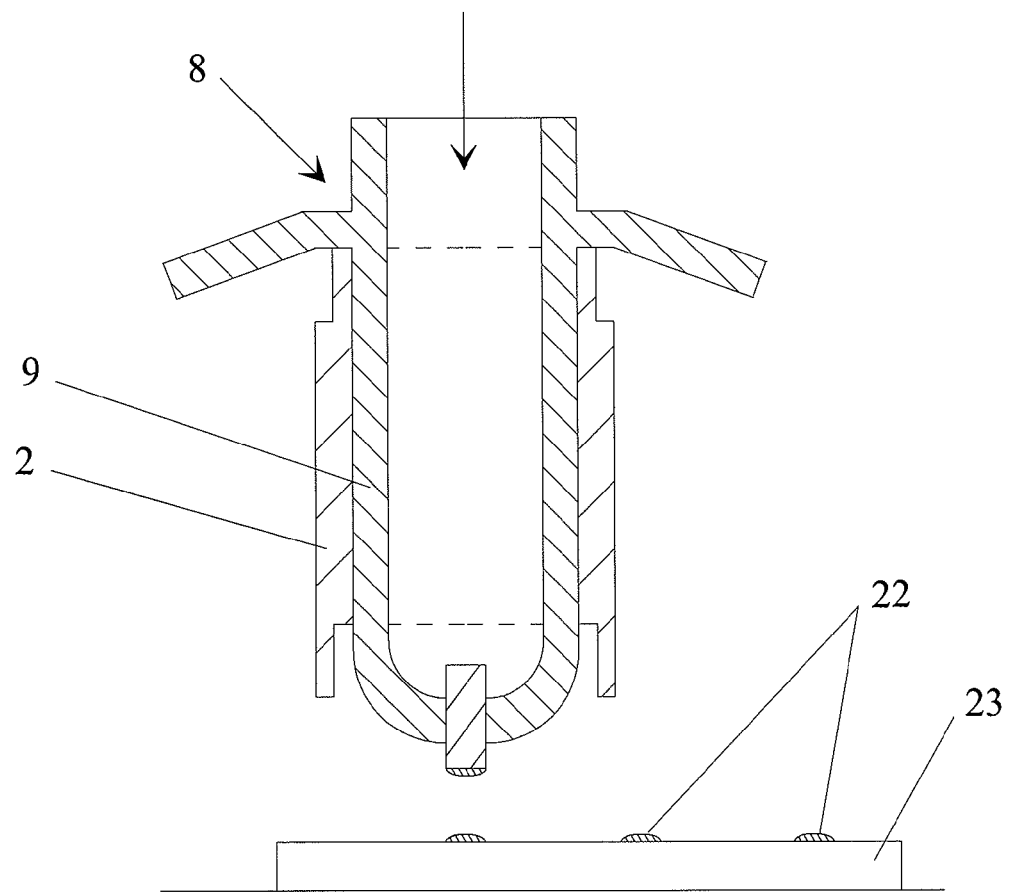
FIG. 8 shows the stamping of concentrated cell material onto a slide.

Again placed on a work-plate 21 and after the removal of the filtrate 20, the cylinder 2 with the filter device 8 can be screwed off the bottom part 3, as shown in FIG. 7. After that, the filter device 8 surrounded by the cylinder 2 is ready for the production of thin-layer prints 22 on slides 23, as shown in FIG. 8. During the filtration process, an amount of cell material is collected regularly on the filter surface 13 which is sufficient for 6-9 thin-layer prints 22 of a diameter of 7 mm to 8 mm.

Figure 9:
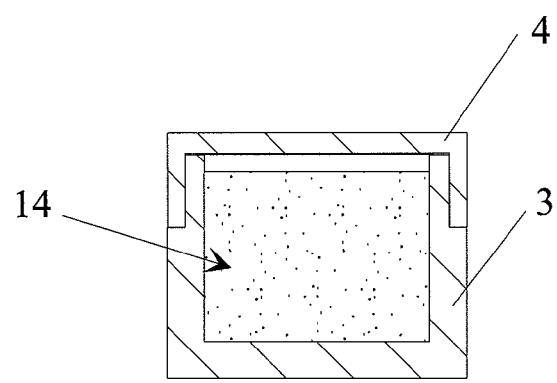
FIG. 9 shows the bottom part, closed by a cap.

After closing the bottom part 3 with the cap 4, as shown in FIG. 9, the liquid, including the cell material still contained in the bottom part 3, can be stored for further investigations or provided for bio-molecular diagnostic testing based on DNA-or mRNA tests.

While there have been shown and described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A device for transportation and preparation of cell material in a liquid for diagnostic purposes, comprising:
   a cylinder having a first open end and a second open end;
   a liquid-tight twist cap configured to close the first open end of the cylinder with a liquid-tight seal; and
   a removable twist bottom part configured to connect to the second open end of the cylinder to form a liquid-tight seal;
   wherein the twist cap is further configured to connect to the bottom part by screwing to form a liquid-tight seal;
   the device further comprising a filter device comprising:
      a tube to radially fit into the cylinder, the tube having a first, open end, and a second open end outwardly rounded with respect to the tube; and
      a filter closing the second open end of the tube, the filter extending at least partly out of the tube.

2. The device according claim 1, wherein an axial depth of penetration and a geometry of the second open end of the filter device closed by the filter is configured such that after the insertion of the filter device, the level of the liquid and the cell material in the bottom part of the cylinder is below the connection of the bottom part the cylinder.

3. The device according claim 2, further comprising:
   a radially overlapping ring-shoulder at the first open end of the tube.

4. The device according to claim 1, further comprising:
   a radially overlapping ring-shoulder at the first open end of the tube.

5. The device according to claim 1, further comprising:
   liquid within the device;
   wherein the bottom part is connected to the second open end of the cylinder, and
   the liquid-tight twist-cap is screwed onto the first open end of the cylinder to close the device.

6. The device according to claim 1, comprising plastic.

* * * * *